(12) United States Patent
Pederson et al.

(10) Patent No.: US 7,820,843 B2
(45) Date of Patent: Oct. 26, 2010

(54) CHELATING CARBENE LIGAND PRECURSORS AND THEIR USE IN THE SYNTHESIS OF METATHESIS CATALYSTS

(75) Inventors: Richard L. Pederson, San Gabriel, CA (US); Jason K. Woertink, Pasadena, CA (US); Christopher M. Haar, Pasadena, CA (US); David E. Gindelberger, South Pasadena, CA (US); Yann Schrodi, Los Angeles, CA (US)

(73) Assignee: Materia, Inc., Pasadena, CA (US)

( * ) Notice: Subject to any disclaimer, the term of this patent is extended or adjusted under 35 U.S.C. 154(b) by 0 days.

(21) Appl. No.: 12/333,125

(22) Filed: Dec. 11, 2008

(65) Prior Publication Data

US 2009/0088581 A1     Apr. 2, 2009

Related U.S. Application Data

(63) Continuation of application No. 11/853,598, filed on Sep. 11, 2007, now abandoned, and a continuation of application No. 11/344,637, filed on Jan. 31, 2006, now Pat. No. 7,268,242, and a continuation of application No. 10/665,734, filed on Sep. 16, 2003, now Pat. No. 7,026,495, and a continuation of application No. 10/295,773, filed on Nov. 15, 2002, now Pat. No. 6,620,955.

(60) Provisional application No. 60/334,781, filed on Nov. 15, 2001.

(51) Int. Cl.
C07F 15/00 (2006.01)
B01J 31/00 (2006.01)

(52) U.S. Cl. .............................. 556/22; 556/136; 549/3; 549/209; 546/4; 546/103; 544/181

(58) Field of Classification Search ................. 556/136, 556/22; 549/3, 209; 546/4, 103; 544/181
See application file for complete search history.

(56) References Cited

U.S. PATENT DOCUMENTS

| | | | |
|---|---|---|---|
| 5,312,940 | A | 5/1994 | Grubbs et al. |
| 5,969,170 | A | 10/1999 | Grubbs et al. |
| 6,111,121 | A | 8/2000 | Grubbs et al. |
| 6,215,019 | B1 | 4/2001 | Pederson et al. |
| 6,306,987 | B1 | 10/2001 | Van Der Schaaf et al. |
| 6,620,955 | B1 | 9/2003 | Pederson et al. |
| 7,026,495 | B1 | 4/2006 | Pederson et al. |
| 7,268,242 | B2 | 9/2007 | Pederson et al. |
| 2002/0107138 | A1 | 8/2002 | Hoveyda et al. |

FOREIGN PATENT DOCUMENTS

WO   1999/51344   10/1999

WO   2000/71554   11/2000

OTHER PUBLICATIONS

Kingsbury et al., J. Am. Chem. Soc., vol. 121, No. 4, pp. 791-799 (1999).*
Randl et al., Synlett, No. 3, pp. 430-432 (2001).*
Braddock et al., Tetrahedron Letters, vol. 43, pp. 3305-3308 (2002).*
"Asarones", The Merck Index, Thirteenth Edition, (2001) p. 828.
Chemical Abstracts No. 26:936 (1932).
Annby et al., Journal of Organometallic Chemistry, vol. 368, No. 3, pp. 295-302 (1989) (Abstract).
The Development of L2X2Ru=CHR Olefin Metathesis Catalysts: An Organometellic Success Story (Tina M. Trnka and Robert H. Grubbs); Jun. 20, 2000.
Comparative Investigation of Ruthenium-Based Metathesis Catalysts Bearing N-Heterocyclic Carbene (NHC) Ligands (Alois Fiirstner et al.); 2001.
Ru-Catalyzed Rearrangement of Styrenyl Ethers. Enantipselective Synthesis of Chromenes through Zr-and Ru-Catalyzed Processes; (Harrity et al.); Oct. 23, 1996.
A Recyclable Ru-Based Metathesis Catalyst; (Kingsbury et al.); Sep. 9, 1998.
New Approaches to Olefin Cross-Metathesis; (Blackwell et al.); Aug. 23, 1999.
Synthesis of Functionalized Olefins by Cross and Ring-Closing Metathesis; (Chatterjee et al); Nov. 11, 1999.
Efficient and Recyclable Monomeric and Dendritic Ru-Based Metathesis Catalysts; (Garber et al.); Apr. 4, 2000.
Cross-metathesis reaction. Generation of highly functionalized olefins from unsaturated alcohols; (J. Cossy et al.); accepted Dec. 6, 2000.

(Continued)

*Primary Examiner*—Porfirio Nazario Gonzalez
(74) *Attorney, Agent, or Firm*—Mark L. Warzel

(57) ABSTRACT

Chelating ligand precursors for the preparation of olefin methathesis catalysts are disclosed. The resulting catalysts are air stable monomeric species capable of promoting various methathesis reactions efficiently, which can be recovered from the reaction mixture and reused. Internal olefin compounds, specifically beta-substituted styrenes, are used as ligand precursors. Compared to terminal olefin compounds such as unsubstituted styrenes, the beta-substituted styrenes are easier and less costly to prepare, and more stable since they are less prone to spontaneous polymerization. Methods of preparing chelating-carbene methathesis catalysts without the use of CuCl are disclosed. This eliminates the need for CuCl by replacing it with organic acids, mineral acids, mild oxidants or even water, resulting in high yields of Hoveyda-type methathesis catalysts. The invention provides an efficient method for preparing chelating-carbene metathesis catalysts by reacting a suitable ruthenium complex in high concentrations of the ligand precursors followed by crystallization from an organic solvent.

23 Claims, No Drawings

OTHER PUBLICATIONS

March's Advanced Organic Chemistry Reactions, Mechanisms, and Structure; (Smith et al.), 5th Edit ion, J. Wiley & Sons, 2001.

Synthesis and Activity of a New Generation of Ruthenium-Based Olefin Metathesis Catalysts Coordinated with 1,3- Dimesityl-4,5-dihydroimidazol-2-ylidene Ligands. Organical Letters, vol. 1, No. 6., pp. 953-956 (1999).

A Convenient Method for Removing All Highly-Colored Byproducts Generated during Olefin Metathesis Reactions; (Paquette et al.); Feb. 18, 2000.

A Convenient Method for the Efficient Removel of Ruthenium Byproducts Generated during Olefin Metathesis Reactions; (Ahn et al.); Mar. 8, 2001.

Purification Technique for the Removal of Ruthenium from Olefin Metathesis Reaction Products; (Heather D. Maynard and Robert H. Grubbs); accepted Mar. 30, 1999.

Komplexverbindung des Rutheniums der allgenmeinen Strukturformel 1, (WO 99/51344; PCT/EP99/01785), (1999).

Chromenes through Metal-Catalyzed Reactions of Styrenyl Ethers. Mechanism and Utility in Synthesis; (Harrity et al.); Nov. 20, 1997.

Garber et al., J. Am. Chem. Soc., vol. 122, No. 34, pp. 8168-8179 (Aug. 30, 2000).

* cited by examiner

CHELATING CARBENE LIGAND PRECURSORS AND THEIR USE IN THE SYNTHESIS OF METATHESIS CATALYSTS

RELATED APPLICATIONS

This application is a continuation of U.S. patent application Ser. No. 11/853,598, filed Sep. 11, 2007, which is a continuation of U.S. patent application Ser. No. 11/344,637, filed Jan. 31, 2006 (now U.S. Pat. No. 7,268,242), which is a continuation of U.S. patent application Ser. No. 10/665,734 filed Sep. 16, 2003, (now U.S. Pat. No. 7,026,495) which is a continuation of U.S. patent application Ser. No. 10/295,773 filed Nov. 15, 2002, (now U.S. Pat. No. 6,620,955) which claims the benefit of U.S. Provisional Application No. 60/334,781 filed on Nov. 15, 2001.

BACKGROUND OF THE INVENTION

Well-defined transition metal carbene complexes have emerged as the catalysts of choice for a wide variety of selective olefin metathesis transformations [F. Z. Dörwald, *Metal Carbenes in Organic Synthesis*; Wiley VCH, Weinheim, 1999]. These transformations include olefin cross metathesis (CM), ring-opening metathesis (ROM), ring-opening metathesis polymerization (ROMP), ring-closing metathesis (RCM), and acyclic diene metathesis (ADMET) polymerization [K. J. Ivin and J. C. Mol, *Olefin Metathesis and Metathesis Polymerization*; Academic Press, London, 1997]. Of particular importance has been the development of ruthenium carbene catalysts demonstrating high activity combined with unprecedented functional group tolerance [T. M. Trnka and R. H. Grubbs, *Acc. Chem. Res.*, 2001, 34, 18-29]. Olefin metathesis serves as a key reaction for the development of a range of regioselective and stereoselective processes. These processes are important steps in the chemical synthesis of complex organic compounds and polymers and are becoming increasingly important in industrial applications. [see for example Pederson and Grubbs U.S. Pat. No. 6,215,019].

An initial concern about using ruthenium olefin metathesis catalysts in commercial applications has been reactivity and catalyst lifetime. The original breakthrough ruthenium catalysts were primarily bisphosphine complexes of the general formula $(PR_3)_2(X)_2Ru=CHR'$ wherein X represents a halogen (e.g., Cl, Br, or I), R represents an alkyl, cycloalkyl, or aryl group (e.g., butyl, cyclohexyl, or phenyl), and R' represents an alkyl, alkenyl, or aryl group (e.g., methyl, $CH=CMe_2$, phenyl, etc.). Examples of these types of catalysts are described in U.S. Pat. Nos. 5,312,940, 5,969,170 and 6,111,121. Though they enabled a considerable number of novel transformations to be accomplished, these bisphosphine catalysts can exhibit lower activity than desired and, under certain conditions, can have limited lifetimes.

More recent developments of metathesis catalysts bearing a bulky imidizolylidine ligand [Scholl et. al. *Organic Letters* 1999, 1, 953-956] such as 1,3-dimesitylimidazole-2-ylidenes (IMES) and 1,3-dimesityl-4,5-dihydroimidazol-2-ylidenes (sIMES), in place of one of the phosphine ligands have led to greatly increased activity and stability. For example, unlike prior bisphosphine complexes, the various imidizolyidine catalysts effect the efficient formation of trisubstituted and tetrasubstituted olefins through catalytic metathesis. Examples of these types of catalysts are described in PCT publications WO 99/51344 and WO 00/71554. Further examples of the synthesis and reactivity of some of these active ruthenium complexes are reported by A. Fürstner, L. Ackermann, B. Gabor, R. Goddard, C. W. Lehmann, R. Mynott, E Stelzer, and O. R. Theil, *Chem. Eur. J.*, 2001, 7, No. 15, 3236-3253; S. B. Gaber, J. S. Kingsbury, B. L. Gray, and A. H. Hoveyda, *J. Am. Chem. Soc.*, 2000, 122, 8168-8179; Blackwell H. E., O'Leary D. J., Chatterjee A. K., Washenfelder R. A., Bussmann D. A., Grubbs R. H. *J. Am. Chem. Soc.* 2000, 122, 58-71; Chatterjee, A. K., Morgan J. P., Scholl M., Grubbs R. H. *J. Am. Chem. Soc.* 2000, 122, 3783-3784; Kingsbury, J. S.; Harrity, J. P. A.; Bonitatebus, P. J.; Hoveyda, A. H. *J. Am. Chem. Soc.* 1999, 121, 791-799; Harrity, J. P. A.; Visser, M. S.; Gleason, J. D.; Hoveyda, A. H. *J. Am. Chem. Soc.* 1997, 119, 1488-1489; and Harrity, J. P. A.; La, D. S.; Cefalo, D. R.; Visser, M. S.; Hoveyda, A. H. *J. Am. Chem. Soc.* 1998, 120, 2343-2351.

The improvements in catalyst activity and expansion of potential substrates resulted in the ruthenium metathesis systems becoming attractive candidates for use in industrial scale processes. In particular, many of the targeted products of olefin metathesis are useful as intermediates in flavors and fragrances, pharmaceuticals and other fine chemicals. Thus, a second major concern has involved ruthenium residues that may be present in the products produced by metathesis. To address this issue, several catalyst removal techniques have been developed [Maynard and Grubbs in *Tetrahedron Letters* 1999, 40, 4137-4140; L. A. Paquette, J. D. Schloss, I. Efremov, F. Fabris, F. Gallou, J. Mendez-Andino and J. Yang in *Org. Letters* 2000, 2,1259-1261; and Y. M. Ahn; K. Yang, and G. I. Georg in *Org. Letters* 2001, 3, 1411], including that described by Pederson and Grubbs [Pederson and Grubbs, U.S. Pat. No. 6,215,049] which is still the most amenable to large scale reactions. Ruthenium metathesis catalysts with a wide range of reactivity and that could be easily removed from the product were now available.

Further progress towards catalyst selectivity, stability, and removal has been recently published by Hoveyda and others [Kingsbury, J. S.; Harrity, J. P. A.; Bonitatebus, P. J.; Hoveyda, A. H. *J. Am. Chem. Soc.* 1999, 121, 791-799] with the demonstration of new, readily recyclable catalyst systems containing chelating carbene species (Scheme 1) that are exceptionally stable and can even be purified by column chromatography in air. For example, the tricyclohexylphosphine-ligated variant, Catalyst 601 (Scheme 1), can be recovered in high yield from the reaction mixture by simple filtration through silica. Hoyveda and coworkers also demonstrated [Cossy, J.; BouzBouz, S.; Hoveyda, A. H. *J. Organometallic Chemistry* 2001, 624, 327-332] that by replacement of the phosphine with the sIMES ligand, Catalyst 627 (Scheme 1) actively promotes the cross-metathesis of acrylonitrile and terminal olefins in moderate to excellent yields (20% to 91%) with a cis to trans olefin ratios that range from 2:1 to over 9:1. Related chelating carbene catalysts are described in US Patent Application Publication No. 2002/0107138 and U.S. Pat. No. 6,306,987.

Scheme 1

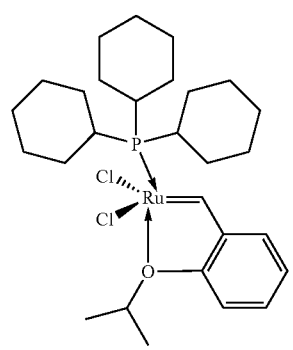

Catalyst 601

-continued

Catalyst 627

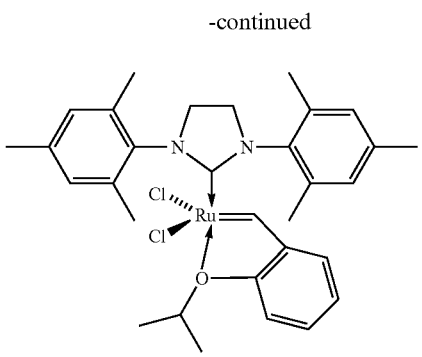

Prior methods used to make these chelating carbene complexes include treating (Ph₃P)₃RuCl₂ with the appropriate diazo species at low temperatures or treatment of a metathesis-active metal carbene complex with the parent styrene in the presence of CuCl followed by column chromatography (Scheme 2). While both of these methods yield the desired compound, they are difficult to scale up. Maintaining very low temperatures on larger reaction vessels requires expensive equipment, and diazo species are prone to violent decomposition under certain conditions. Using the o-isopropoxy styrene/CuCl route is also not amenable to large scale due to the requirement to purify the product by column chromatography. A further shortcoming includes the use of the Wittig reaction to yield the key styrene intermediate. Wittig reactions are not convenient on a commercial scale because of the high costs of the reagents and the by-product, triphenylphosphine oxide, produces an excessive mass of waste. Alternatives to Wittig reactions would include Heck, Stille or Suzuki coupling of vinyl trialkyltin, vinyl triflates or vinyl borate; respectively, to a halo-phenol substrate. These starting materials are generally expensive, and the reactions with trialkyl tin reagents involve toxic compounds which require special waste disposal procedures. Finally the styrene itself is prone to polymerization under some of the conditions required to make the "Hoveyda-type" catalysts. Therefore, there is a need for an efficient and economical synthesis to chelating carbene type ruthenium metathesis catalysts in larger quantities.

Scheme 2

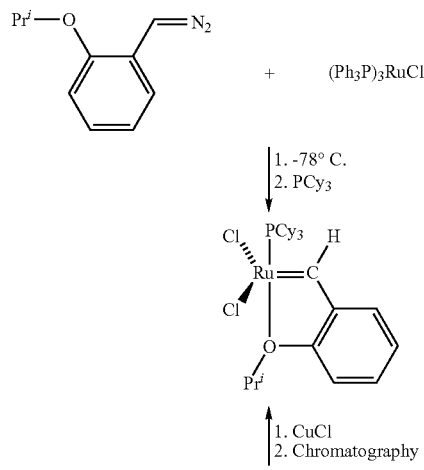

-continued

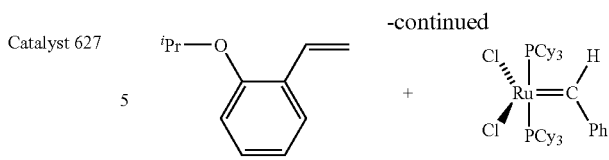

The present invention describes efficient and versatile routes to useful and valuable Hoveyda-type catalysts with chelating phenyl carbene ligands while eliminating expensive and toxic reagents. The present invention describes the synthesis of substituted olefins that are precursors to catalyst complexes and their use as reagents to prepare olefin metathesis catalysts with chelating carbene ligands.

SUMMARY OF THE INVENTION

The present invention comprises methods for the use of novel chelating ligand precursors for the preparation of olefin metathesis catalysts. The resulting catalysts comprise monomeric species which are air stable, are capable of promoting various forms of metathesis reactions in a highly efficient manner, and can be recovered from the reaction mixture and reused.

One embodiment of the present invention is the use of internal olefin compounds, specifically beta-substituted styrenes, as ligand precursors instead of terminal olefin compounds such as unsubstituted styrenes (Scheme 3). Although internal olefins tend to be less reactive than terminal olefins, we have surprisingly found that the beta-substituted styrenes are sufficiently reactive to efficiently produce the desired catalyst complexes. Compared with the styrene compounds, the beta-substituted styrenes are much easier and less costly to prepare in large quantities and are more stable in storage and use since they are less prone than terminal styrenes to spontaneous polymerization.

Scheme 3

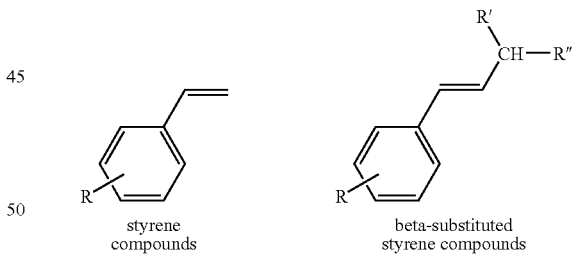

styrene compounds     beta-substituted styrene compounds

Another embodiment of the present invention are methods of preparing chelating-carbene metathesis catalysts without the use of CuCl as previously required. In previous reports, CuCl was used to sequester phosphine ligands which shifts the equilibrium of metathesis reactions to product formation. The use of CuCl in large scale synthesis is problematic in that the resulting metathesis catalyst must be purified by chromatography before recrystallization, requiring large volumes of silica and solvent [Kingsbury et. al. *J. Am. Chem. Soc.* 1999, 121, 791-799]. The present invention eliminates the need for CuCl by replacing it with organic acids, mineral acids, mild oxidants or even water, resulting in high yields of Hoveyda-type metathesis catalysts. The phosphine byproduct is removed by an aqueous wash or filtration, thereby eliminating the chromatography step and allowing catalysts to be readily isolated by crystallization from common organic solvents.

A further embodiment of the present invention is an efficient method for preparing chelating-carbene metathesis catalysts by reacting a suitable ruthenium complex in high concentrations of the novel ligand precursors followed by crystallization from an organic solvent. For example, in this manner Catalyst 601 can be simply isolated by filtering a hexane solution of the reaction mixture resulting from the reaction of neat ligand precursor and a ruthenium carbene complex. By using the beta-substituted styrene derivatives, the excess, unreacted ligand is recoverable from such reaction mixtures and can be reused. This is difficult with the parent styrenes due to the propensity of those materials to polymerize under reaction and workup conditions.

DETAILED DESCRIPTION OF THE INVENTION

The present invention describes the synthesis of "Hoveyda-type" chelating carbene metathesis catalysts from the cross metathesis of novel ligand precursors and metal carbene complexes. Although any metathesis-active metal carbene complex is suitable for use in the present invention, preferred metal complexes include the Grubbs-type compounds described in U.S. Pat. Nos. 5,312,940, 5,969,170, 6,111,121 and 6,426,419 and PCT publications WO 99/51344 and WO 00/71554. These complexes have the general formula $X^1X^2L^1L^2M=CR^1R^2$, wherein $X^1$ and $X^2$ are each, independently, any anionic ligand; $L^1$ and $L^2$ are each, independently, any neutral electron donor ligand; M is ruthenium or osmium; and $R^1$ and $R^2$ are each, independently, hydrogen or a group selected from the group consisting of alkyl, alkenyl, alkynyl, aryl, alkoxy, alkenyloxy, alkynyloxy, aryloxy, alkoxycarbonyl, alkylthio, alkylsulfonyl, alkylsulfinyl and trialkylsilyl, any of which may be optionally substituted with a functional group selected from the group consisting of halogen, alkyl, alkenyl, alkynyl, aryl, heteroaryl, alkoxy, alkenyloxy, aryloxy, alkoxycarbonyl, carbonyl, alkylamino, alkylthio, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, sulfide, disulfide, sulfonate, carbamate, silane, siloxane, phosphine, phosphate, or borate.

The ligand precursors of the present invention are functionalized beta-substituted styrene compounds, which may be conveniently prepared by the isomerization of functionalized allylbenzenes, with the structure shown in Scheme 4.

Scheme 4

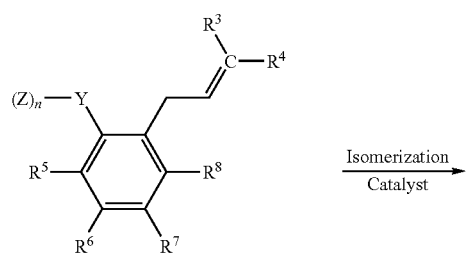

Isomerization Catalyst

-continued

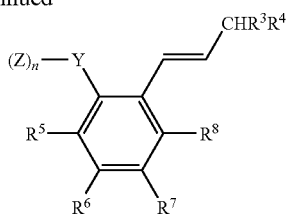

Wherein:

Y is a heteroatom such as oxygen (O), sulfur (S), nitrogen (N), or phosphorus (P);

Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, sulfide, disulfide, carbamate, silane, siloxane, phosphine, phosphate, or borate.

n is 1, in the case of a divalent heteroatom such as O or S, or 2, in the case of a trivalent heteroatom such as N or P;

$R^3$ and $R^4$ are independently selected from the group consisting of hydrogen, $C_1$-$C_{20}$ alkyl, $C_2$-$C_{20}$ alkenyl, $C_2$-$C_{20}$ alkynyl, $C_1$-$C_{20}$ substituted aryl, $C1$-$C_{20}$ functionalized alkyl, $C_2$-$C_{20}$ functionalized alkeneyl, $C_2$-$C_{20}$ functionalized alkenyl, or $C_1$-$C_{20}$ functionalized substituted aryl where the functional group(s) may independently be one or more of the following: alkoxy, aryloxy, halogen, carboxylic acid, ketone, aldehyde, nitrate, cyano, isocyanate, hydroxyl, ester, ether, amine, imine, amide, sulfide, disulfide, carbamate, silane, siloxane, phosphine, phosphate, or borate;

$R^5$, $R^6$, $R^7$, and $R^8$ are each, independently, selected from the group consisting of hydrogen, halogen, alkyl, alkenyl, alkynyl, aryl, heteroaryl, alkoxy, alkenyloxy, aryloxy, alkoxycarbonyl, carbonyl, alkylamino, alkylthio, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, sulfide, disulfide, sulfonate, carbamate, silane, siloxane, phosphine, phosphate, or borate. Additionally, any two or more of $R^5$, $R^6$, $R^7$, and/or $R^8$ may be independently connected through hydrocarbon or functionalized hydrocarbon groups forming aliphatic or aromatic rings. Furthermore, one who is skilled in the art will recognize that $R^8$ should be chosen such that its steric bulk or chemical functionality does not interfere with the cross-metathesis reaction between the ligand precursor and the metal carbene complex.

Preferred ligand precursors are beta-methyl styrenes wherein Y is oxygen or sulfur; n is 1; Z is alkyl, aryl or trialkylsilyl; and $R^3$ and $R^4$ are both hydrogen. Particularly preferred ligand precursors are alkoxy-substituted beta-methyl styrenes wherein Y is oxygen; n is 1; Z is methyl, isopropyl, sec-butyl, t-butyl, neopentyl, benzyl, phenyl or trimethylsilyl; and $R^3$, $R^4$, $R^5$, $R^6$, $R^7$ and $R^8$ are all hydrogen. Examples of particularly preferred ligand precursors of these types include 2-methoxy-β-methylstyrene, 2-isopropoxy-β-methylstyrene and 2-isopropoxy-3-phenyl-β-methylstyrene:

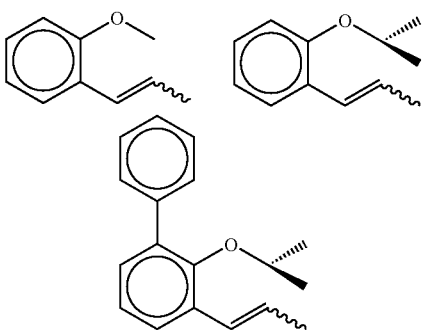

The precursor compounds for chelating ligands are easily prepared in high yields from commercially available starting materials. Treatment of allyl aryl compounds with an isomerization catalyst cleanly migrates the double bond one carbon closer to the aryl ring forming a beta-substituted styrenic olefin (Scheme 4). We have found that (PPh$_3$)$_3$RuCl$_2$ is a preferred, highly active isomerization catalyst that is effective at amounts ranging from about 0.001 to 20 mole percent relative to the allyl aryl compound. It is preferable to isomerize the allylphenol compounds prior to further functionalization, since the hydroxy protons serve to activate the catalyst and the reactions can therefore be run neat. For other compounds without their own protic source, it is necessary to add an alcohol or other proton source to initiate the isomerization catalysis. From the structures shown in Scheme 4, one skilled in the art can appreciate the diversity of substitution on the aromatic system that can be achieved. This allows the ligand to be fine-tuned for specific applications. For the case where Y is oxygen, a wide variety of allyl phenol starting materials are easily produced by the Claisen rearrangement (Scheme 5) of allylic aryl ethers [March's Advanced Organic Chemistry; 5$^{th}$ Edition, Eds. M. B. Smith and J. March; John Wiley and Sons, New York, N.Y. 2001, pp. 1449-1452]. Similar rearrangements are operative for the case where Y is nitrogen, although more forcing conditions are typically required.

Scheme 5

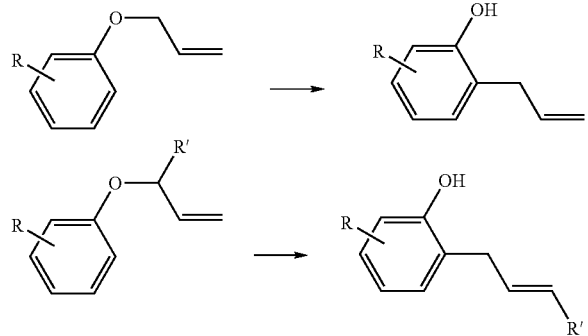

The above described ligand precursors can be used to prepare metathesis catalysts with a chelating carbene group. In the most basic practice of the present invention, as with the parent styrenes, it is possible to mix a metathesis active metal carbene complex with the ligand precursor in a suitable solvent to effect the transformation. Preferred solvents typically include, but are not limited to, chlorinated solvents (such as methylene chloride, dichloroethane, chlorobenzene, and dichlorobenzenes), ethereal solvents (such as tetrahydrofuran or dioxane), aromatic solvents (such as benzene, toluene, or xylenes), and hydrocarbon solvents (such as hexanes, heptane, and petroleum distillate fractions). In general, at least one equivalent, and preferably an excess amount, of the ligand precursor is utilized. Depending upon the reactivity of the metathesis-active metal carbene complex, the reaction may proceed at room temperature, or even lower, or may need to be heated. As the progress of these reactions can be conveniently monitored by a variety of techniques including thin-layer chromatography (TLC), those skilled in the art can readily ascertain the appropriate conditions of time and temperature to achieve high conversions to the desired chelating carbene complexes.

In general, these reactions proceed more slowly and/or require somewhat higher reaction temperatures than comparable reactions with terminal styrenes. In order to increase the reaction rates and achieve higher conversion, high ratios of ligand precursor to metal carbene complex can be utilized. In fact, in the practice of the present invention, the reaction can be performed using neat ligand precursor as the solvent. In general, five to ten mole-equivalents of ligand precursor will give reasonable reaction rates and high conversions. This approach cannot be utilized with the terminal styrene ligand precursors due to their propensity to spontaneously polymerize under the reaction conditions. Upon completion of the reaction, the ligand precursor can be distilled off of the reaction mixture and the chelating carbene product recrystallized from an appropriate solvent. Alternatively, the chelating carbene product can be precipitated by the addition of an appropriate nonsolvent and the unreacted ligand precursor recovered by distillation of the mother liquor. The beta-substituted styrene compounds are sufficiently robust so that high recoveries can be achieved by these methodologies, which would not be practical with the easily polymerized terminal styrenes.

In general, treatment of one mass equivalent of a ruthenium carbene complex with between 1 and 20 mass eqivalents of ligand precursor in the presence of an optional co-solvent (generally between about 1-20 mass equivalents relative to the ruthenium complex) yields a thick mixture that gradually looses viscosity during the course of the reaction. Optionally the mixture can be heated or cooled. The mixture may also be exposed to a static or dynamic vacuum. The reaction is preferably conducted under an inert atmosphere but may be conducted in air unless the metal carbene complex is particularly air-sensitive. After 3-120 hours of stirring, the reaction is usually complete and the product may be isolated as described above.

A complementary method for increasing reaction rates and conversion utilizes an additive to sequester the ligand that is displaced from the metal carbene complex during the course of the reaction. When the displaced ligand is a phosphine ligand, as is typical, the sequestering agent that has been commonly used in cuprous cloride (CuCl), although this is difficult to separate from the product without using chromatograhy which is impractical at large scale. Suprisingly, we have found that replacement of the CuCl with mineral acids, organic acids or mild oxidants in the presence of the ligand precursors of the present invention is also very effective. Treatment of ruthenium carbene complexes with between 1 to 10 equivalents of ligand precursor and between 0.1 to 10 equivalents acid or mild oxidant yields the new catalyst containing the chelating carbene moiety. After the reaction is complete, the displaced ligand and the sequestering agent can be readily removed from the mixture by extraction into water. The product can then be simply crystallized from the resulting solution in organic solvents in very high yield, eliminating the need for column chromatography. Preferred sequestering agents include hydrochloric acid, solutions of hydrogen chloride in ethereal solvents (such as diethyl ether, tetrahydrofuran, or dioxane), gaseous hydrogen chloride dissolved in the reaction mixture, glacial acetic acid, bleach, and dissolved oxygen. Water can be utilized as a sequestering agent for particularly basic ligands such as tricyclohexylphosphine (TCHP or $PCy_3$). The use of sequestering agents is particularly preferred when using very robust metal carbene complexes such as those containing IMES or sIMES ligands. When using less robust complexes such as ruthenium carbenes ligated with two phosphine ligands, greater care is needed and it is desirable to utilize the mildest sequestering agents or to slowly add the sequestering agents over the course of the reaction.

EXAMPLES

Example 1

Synthesis of o-hydroxy beta-methyl styrene [1] from 2-allylphenol

To a dry 100 mL round-bottom flask containing a magnetic stirbar was added 25 g (186 mmol) of 2-allylphenol (Aldrich). The flask was sparged with argon for 30 minutes, followed by the addition of 71 mg (0.05 mol %) of $(PPh_3)_2Cl_2Ru$, a highly effective double-bond isomerization catalyst, and then heated to 70° C. for 17.5 hours. GC analysis* indicated >99% conversion of 2-allyl phenol to o-hydroxy beta-methyl styrene. GC results show ortho-hydroxy beta-methyl styrene $R^t$ 8.51 minutes and $R^t$ 11.13 minutes (Z and E isomers), and 2-allylphenol $R^t$ 8.86 minutes. The catalyst was removed with tris-hydroxymethyl phosphine (THP), as previously described by Pederson and Grubbs [U.S. Pat. No. 6,219,019], to yield 25 g, quantitative yield. Isomeric ratio of E:Z isomers was 45:55.

*GC Analysis: HP 5890 GC with DB 225 capillary GC column (30 m×0.25 mm ID×0.25 um film thickness) Head pressure 15 psi, FID detection. Method: 100° C. for 1 minute then 10° C./minute to 210° C. for 6 minutes.

Example 2

Synthesis of ortho-Isopropoxy beta-Methyl Styrene [2]

Protection of an aromatic hydroxyl group with isopropyl was as described by T. Sala and M. V. Sargent, *J. Chem. Soc., Perkin Trans.* 1, 2593, (1979). To a dry 500 mL round-bottom flask containing a magnetic stirbar was added 50 g (373 mmol) of ortho-hydroxy beta-methyl styrene, 57.3 g (466 mmol) isopropyl bromide, 300 mL of anhydrous dimethylformamide (DMF), and 64 g (466 mmol) $K_2CO_3$. The heterogeneous mixture was warmed to 60° C. After 9 hours the reaction was 57% converted, 30 g (244 mmol) isopropyl bromide and 32 g (232 mmol) of $K_2CO_3$ was added, and stirring was continued. After 48 hours, GC analysis indicated >98% conversion to ortho-isopropoxy beta-methyl styrene. GC results: ortho-hydroxy beta-methyl styrene $R^t$ 8.51 minutes and $R^t$ 11.13 minutes (Z and E isomers), ortho-isopropoxy beta-methyl styrene $R^t$ 7.35 minutes (Z-isomer) and $R^t$ 8.30 minutes (E-isomer).

The reaction was cooled to room temperature and 200 mL of water and 100 mL of tertiary-butyl methyl ether (TBME) were added and mixed. The phases were separated and the aqueous phase was washed with another 100 ml of TBME. The organic phases were combined and washed with 2×100 mL of water, dried with anhydrous sodium sulfate, filtered and concentrated under reduced pressure to yield crude ortho-isopropoxy beta-methyl styrene. Vacuum distillation ($Bpt_{1.0}$ 60° C. to 65° C.) yielded 61.3 g (348 mmol) or 93% isolated yield.

$^1$H NMR (300 MHz) $CDCl_3$ δ: 7.8 (d, 1H aromatic), 7.5 (m, 1H, aromatic), 6.90 (bt, 2H, aromatic), 6.4 (dd, 1H, Ph—CH=CH), 6.0 (m, 1H, Ph—CH=CHCH$_3$), 4.64 (m, 1H, CH(CH$_3$)$_2$), 1.35 (J 6.3 Hz, 6H, CH(CH$_3$)$_2$). $^{13}$C NMR (75 MHz) $CDCl_3$ δ: 130.23, 127.68, 127.52, 126.36, 125.99, 125.71, 125.53, 120.59, 119.92, 114.08, 113.96, 70.58, 22.298, 19.09, 14.87.

Example 3

Alternative Synthesis of ortho-Isopropoxy beta-Methyl Styrene [2]: Synthesis of ortho-Isopropoxy Salicylaldehyde [3]

Similar to the procedure of Example 2, 6.5 g (53.2 mmol) of salicylaldehyde, 100 mL of anhydrous DMF, 6.5 g of $K_2CO_3$, and 10 g of isopropyl bromide (81.3 mmol) were added to a dry 250 mL round-bottom flask containing a magnetic stirbar. The heterogeneous mixture was stirred with heating to 60° C. for 24 hours when GC analysis indicated complete conversion to o-isopropoxy salicylaldehyde. Water 100 mL was added and the organics were washed with 2×100 mL of TBME, the TBME phases were combined and washed with 2×50 mL water, dried with anhydrous sodium sulfate, filtered and concentrated to yield [3] (8.3 g, 95% yield). Salicylaldehyde $R^t$ 6.473 minutes, ortho-isopropoxy salicylaldehyde $R^t$ 10.648 minutes. $^1$H NMR (300 MHz) $CDCl_3$ δ: 10.46 (CHO), 7.8 (d, 1H aromatic), 7.5 (m, 1H, aromatic), 6.90 (t, 2H, aromatic), 4.64 (m, 1H, CH(CH$_3$)$_2$), 1.35 (J 6.3 Hz, 6H, CH(CH$_3$)$_2$).

Example 4

Alternative Synthesis of ortho-Isopropoxy beta-Methyl Styrene [2]: Synthesis of ortho-Isopropoxy (2'-Hydroxypropyl) Benzene [4]

To a 50 mL round-bottom flask was added 1 g (7.0 mmol) of [3] and 25 mL of anhydrous tetrahydrofuran (THF). The flask was sparged with Argon while cooling to −15° C. over 15 minutes. Ethyl magnesium chloride (3 mL of 3 M in ether) was added drop wise over 10 minutes. The reaction was warmed to room temperature and quenched with water-saturated ammonium chloride. GC analysis indicated >99% conversion to ortho-isopropoxy (2'-hydroxypropyl) benzene with $R^t$=10.969 minutes (4.1%) and 11.374 minutes (95.9%), E and Z isomers. The product was isolated by usual methods to yield [4] (1.4 g, quantitative yield). This product was used in the next reaction without further purification.

Example 5

Alternative Synthesis of ortho-Isopropoxy beta-Methyl Styrene [2]

To a 250 mL round-bottom flask was added 1.4 g (7.0 mmol) of [4], 100 mL of anhydrous toluene, and 100 mg of p-toluene sulfonic acid. The mixture was heated to 90° C. for 90 minutes when GC analysis indicated complete conversion to [2] with an isomeric ratio of E:Z isomers of 97:3. $^1$H NMR and $^{13}$C NMR were in agreement with previously synthesized material.

Example 6

Synthesis of [(sIMES)(o-isopropoxyphenylmethylene) Ruthenium Dichloride] from (sIMES)(PCy$_3$) Cl$_2$Ru=CHPh [5] and CuCl To a dry 100 mL round-bottom flask containing a magnetic stirbar, under argon, was added 1.79 g (2.1 mmol, 1.0 equiv) [5], CuCl (521 mg, 5.28 mmol, 2.51 equiv), and 25 mL of anhydrous CH$_2$Cl$_2$. Ligand precursor [2] (403 mg, 2.1 mmol, 1.0 equiv) was added to the reddish solution in 20 mL of CH$_2$Cl$_2$ at room temperature. A reflux condenser was added and the mixture was heated for 70 minutes, under argon. The crude product was concentrated and loaded onto silica gel and eluted with 2:1 pentane:CH$_2$Cl$_2$ then 1:1 pentane:CH$_2$Cl$_2$ to remove a dark green band. The column was washed with CH$_2$Cl$_2$, then Et$_2$O. The green and yellow bands were combined and concentrated under reduced pressure to yield a dark green solid. The solvents are removed under reduced pressure and the solid was crystallized from hexane to yield 1.07 g (1.70 mmol, 85%) of [6]. $^1$H NMR (300 MHz, CDCl$_3$) δ: 16.56 (s, 1H, Ru=CHAr), 7.48 (m, 1H, aromatic CH), 7.07 (s, 4H, mesityl aromatic CH), 6.93 (dd, J=7.4 Hz, 1.6 Hz, 1H, aromatic CH), 6.85 (dd, J=7.4 Hz, 1H, aromatic CH), 6.79 (d, J=8.6 Hz, 1 H, aromatic CH) 4.90 (septet, J=6.3 Hz, 1H, (CH$_3$)$_2$CHOAr), 4.18 (s, 4H, N(CH$_2$)$_2$N), 2.48 (s, 12 H, mesityl o-CH$_3$), 2.40 (s, 6H, mesityl p-CH$_3$), 1.27 (d, J=5.9 Hz, 6H, (CH$_3$)$_2$CHOAr. $^{13}$C NMR (75 MHz, CDCl$_3$) δ: 296.8 (q, J=61.5 Hz), 211.1, 152.0, 145.1, 145.09, 138.61, 129.4 (d, $^J$NC 3.9 Hz), 129.3, 129.2, 122.6, 122.1, 122.8, 74.9 (d, $^J$OC 10.7 Hz), 51.4, 30.9, 25.9, 21.01.

Example 7

Synthesis of [6] from [5] and Bleach

To a dry 100 mL round-bottom flask containing a magnetic stirbar was added 1.79 g (2.1 mmol, 1.0 equiv) of [5], 10 mL of household bleach (i.e., aqueous sodium hypochlorite), and 25 mL of CH$_2$Cl$_2$. Ligand precursor [2] (403 mg, 2.1 mmol, 1.0 equiv) was added to the reddish solution in 20 mL of CH$_2$Cl$_2$ at room temperature. A reflux condenser was added and the mixture was heated for 4 hours. The organic phase was washed with water, isolated, neutralized, dried, filtered and concentrated under reduced pressure to yield a green solid. Crystallization from pentane yielded 43% of [6] of acceptable purity as indicated by NMR spectral analysis.

Example 8

Synthesis of [6] from [5] and Ethereal HCl

To a dry 100 mL round-bottom flask containing a magnetic stirbar was added 1.79 g (2.1 mmol, 1.0 equiv) of [5], 25 mL of CH$_2$Cl$_2$, and 2.4 mL of ethereal HCl (2.0 M, 2.0 equiv). Ligand precursor [2] (420 mg, 2.4 mmol, 1.14 equiv) was added to the reddish solution in 20 mL of CH$_2$Cl$_2$ at room temperature. A reflux condenser was added and the mixture was heated for 1 hour. The organic phase was washed with 2×25 mL water, dried with anhydrous sodium sulfate, filtered and concentrated under reduced pressure to yield a green solid. Crystallization from CH$_2$Cl$_2$/hexane yielded [6] (1.03 g, 78% yield) as indicated by NMR spectral analysis.

Example 9

Synthesis of [(PCy$_3$)(o-isoproxyphenylmethylene) Ruthenium Dichloride] [8] from (PCy$_3$)$_2$ Cl$_2$Ru=CHPh [7]

Ruthenium complex [7] (270 g, 0.32 moles) was charged into a 2 L 3-neck roundbottom flask. Ligand precursor [2] (505 g, 2.8 moles) was then added, and one neck of the flask was fitted with a gas adapter, another with a stopper and the third with a distillation head and receiver flask. The flask was placed under vacuum and slowly heated to 80° C. The mixture was maintained at between 65° C. and 70° C. under vacuum for 24 hours. The temperature was raised to 80° C. and the remaining ligand precursor was distilled away. The vacuum was broken and hexanes (1 L) was added to the flask. The reaction mixture was stirred for several minutes then filtered. The solids were washed with warm hexanes (3×100 mL) yielding [8] (96.2 g, 49% yield) as indicated by NMR spectral analysis.

Example 10

Synthesis of [8] from (PCy$_3$)$_2$Cl$_2$Ru=CH—CH=C (CH$_3$)$_2$ [9]

Ruthenium complex [9] (48 g, 0.059 moles) was charged to a 1 L roundbottom flask and ligand precursor [2] was charged along with toluene (400 g). A reflux condensor was attached to the flask and kept at 15° C. The mixture was warmed to 70° C. under vacuum for 12 hours. The condenser was warmed to 45° C. and the toluene was removed in vacuuo. The mixture was then heated to 80° C. for 48 hours under a static vacuum. A distillation head was attached to the flask and the remaining ligand precursor distilled away in vacuo. 500 mL of hexanes was added to the flask and the mixture was allowed to cool to room temperature with mixing. The mixture was filtered and the solids washed with hexanes (100 mL) yielding 16.7 g (46% yield) of [8] as indicated by NMR spectral analysis.

Example 11

Synthesis of [8] from [9] with Hydrochloric Acid

A mixture of methylene chloride (200 g) and ligand precursor [2] (200 g, 1.136 moles) was charged into a roundbottom flask, warmed to 40° C., and degassed by sparging with nitrogen gas. Ruthenium complex [9] (100 g, 0.125 moles) was then added to the mixture against a nitrogen sparge. Hydrochloric acid (6N, 20 mL, 0.120 moles) was added slowly dropwise through an addition funnel over a period of three hours to the stirred mixture, which was maintained at 40° C. under nitrogen. After stirring for an additional hour at 40° C., analysis by thin-layer chromatography (TLC) indicated only partial conversion. The mixture was then stirred for an additional two hours at 50° C. and 1 hour at 60° C. until TLC suggested nearly complete conversion. An additional 5 mL of 6N hydrochloric acid was then added and the mixture stirred for two hours to assure completion. While still warm, 100 mL of methanol was added, and the resulting mixture poured into 1,400 mL of methanol to precipitate the product.

The mixture was filtered and the solids washed and dried to yield 47.5 g (63% yield) of [8] as indicated by TLC analysis.

Example 12

Synthesis of [8] from [9] with Water

A mixture of toluene (200 mL), ligand precursor [2] (100 g, 0.568 moles), ruthenium complex [9] (49 g, 0.061 moles) and water (100 mL) was charged into a roundbottom flask, sparged with nitrogen, and vigorously stirred overnight at 80° C. Analysis by TLC indicated nearly complete conversion. Hydrochloric acid (6N, 10 mL) was then added and the mixture stirred for several minutes to assure completion. The aqueous layer was removed and 400 mL of methanol added to precipitate the product. After stirring overnight, the mixture was filtered and the solids washed with methanol (50 mL), acetone (50 mL) and hexanes (50 mL) and dried to yield 19 g (52% yield) of [8].

Example 13

Synthesis of [6] from [5] and Hydrochloric Acid in THF

Ligand precursor [2] (5.28 g, 0.030 mole) and 50 mL of a mixture of 1 part concentrated hydrochloric acid in 5 parts tetrahydrofuran were added to a dry 500 mL round-bottom flask containing a magnetic stirbar. The mixture was degassed for ten minutes with a nitrogen sparge before 10 g (0.012 mole) of [5] was added. The reaction mixture was then heated to 60° C. for two hours when TLC analysis indicated that conversion was complete. After cooling to room temperature, the product precipitated, was collected by filtration, and washed with methanol to yield 4.33 g of [6] (59% yield). The filtrates were combined and refiltered to yield a second crop of 1.07 g of [6], giving an overall yield of 73%.

Example 14

Synthesis of [6] from [5] and Hydrochloric Acid in THF

Ligand precursor [2] (2.64 g, 0.015 mole) and 30 mL of a mixture of 1 part concentrated hydrochloric acid in 5 parts tetrahydrofuran were added to a dry round-bottom flask containing a magnetic stirbar. The mixture was degassed for ten minutes with a nitrogen sparge before 10 g (0.012 mole) of [5] was added. The reaction mixture was then heated to 60° C. for two hours when TLC analysis indicated that conversion was complete. After cooling to room temperature, 30 mL of distilled water was added to help precipitate the product, which was collected by filtration and washed with methanol to yield 5.37 g of [6] (73% yield).

Example 15

Synthesis of [6] from [5] and Gaseous Hydrogen Chloride

Ligand precursor [2] (84 g, 0.477 mole), [5] (161 g, 0.190 mole), and 1.6 L of methylene chloride were added to a dry roundbottom flask containing a magnetic stirbar and degassed with a nitrogen sparge. Dry hydrogen chloride gas was then bubbled through the mixture for approximately ten seconds. After stirring for two hours, hydrogen chloride gas was again bubbled through the mixture for approximately ten seconds. After a total of five hours of stirring, TLC analysis indicates complete conversion. The reaction mixture was concentrated by rotary evaporation before 500 mL of methanol was added to precipitate the product, which was isolated by filtration and washed twice with 100 mL of methanol to yield 97.5 g (82%) of [6].

Example 16

One-Pot Synthesis of [8] from Dichloro(1,5-cyclooctadiene)ruthenium

Dichloro(1,5-cyclooctadiene)ruthenium (4.0 g, 0.014 moles), tricyclohexylphosphine (8.4 g, 0.030 moles), degassed triethylamine (2 mL), and degassed sec-butanol (60 mL) were combined in a pressure bottle under argon. The pressure bottle was purged with hydrogen gas, pressurized to 60 psi, and the mixture heated to 80° C. for 18 hours (the bottle was repressurized as needed to maintain 60 psi hydrogen). The reaction mixture was then allowed to cool down and the hydrogen gas was vented off. Degassed methanol (60 mL) was added to the orange slurry and the filtrate decanted off via stick filtration under argon to leave an orange solid in the bottle, which was washed with degassed methanol (60 mL). Degassed toluene (60 mL) was added to the orange solid and the orange slurry cooled to 0° C. Degassed 3-chloro-3-methyl-1-butyne (1.7 mL, 0.015 moles) was added dropwise via syringe at 0° C. The orange slurry progressively turned to a maroon slurry, while gas bubbled away. The mixture was stirred at room temperature for 2 hours after addition was complete. Ligand precursor [2] (18 g, 0.102 moles) was then charged and the mixture was heated to 80° C. and sparged with argon for 3 days (degassed toluene was added as needed). The brown slurry was allowed to cool to room temperature and a mixture of 30 mL methanol and 10 mL of concentrated hydrochloric acid was added in air with mixing. After stirring for 15 minutes at room temperature, the two phases were allowed to separate and the methanol phase was decanted off. Trituration with methanol (2×50 mL) gave a solid, which was collected on a frit and washed with more methanol (2×20 mL). The brown solid was then washed with hexanes (2×20 mL) and dried to give [8] (5.1 g, 0.085 moles) in 61% yield.

The invention claimed is:
1. A chelating carbene complex of the formula:

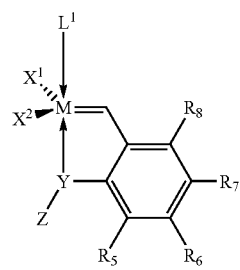

wherein
$X^1$ and $X^2$ are each, independently, any anionic ligand;
$L^1$ is a neutral electron donor, and wherein any of two or three of $X^1$, $X^2$, and $L^1$ may form a multidentate ligand;
M is ruthenium or osmium;
$R^5$, $R^6$, $R^7$, and $R^8$ are each, independently, selected from the group consisting of hydrogen, halogen, alkyl, alkenyl, alkynyl, aryl, heteroaryl, alkoxy, alkenyloxy, aryloxy, alkoxycarbonyl, carbonyl, alkylamino, alkylthio, alkylsulfonyl, nitrile, nitro, alkylsulfinyl, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, and borate, wherein any two of $R^5$, $R^6$, $R^7$, and $R^8$ may be independently connected through hydrocarbon or functionalized hydrocarbon groups forming an aliphatic or aromatic ring;

Y is a heteroatom selected from oxygen (O), sulfur (S), nitrogen (N), or phosphorus (P); and Z is selected from the group consisting of hydrogen, t-butyl, neopentyl, aryl, functionalized alkyl, and functionalized aryl where the functional group(s) may independently be or more or the following: alkoxy, aryloxy, halogen, carboxylic acid, ketone, aldehyde, nitrate, isocyanate, hydroxyl, ester, ether, amine, imine, amide, sulfide, disulfide, carbamate, silane, siloxane, phosphine, phosphate, and borate.

2. The chelating carbene complex of claim 1, wherein the chelating carbene complex is prepared by a method comprising contacting a metathesis-active metal carbene complex with a beta-substituted styrene ligand precursor, wherein the metathesis-active metal carbene complex is of the formula $X^1X^2L^1L^2M=CR^1R^2$, wherein $X^1$, $X^2$, $L^1$, and M are as defined in claim 1;

$L^2$ is any neutral electron donor, and wherein any of two or three of $X^1$, $X^2$, $L^1$, and $L^2$ may form a multidentate ligand; and $R^1$ and $R^2$ are each independently, selected from hydrogen or a substituent selected from the group consisting of alkyl, alkenyl, alkynyl, aryl, alkylcarboxylate, arylcarboxylate, alkoxy, alkenyloxy, alkynyloxy, aryloxy, alkoxycarbonyl, alkylthio, alkylsulfonyl, alkylsulfinyl, or trialkylsilyl, wherein each of the substituents is substituted or unsubstituted, and wherein $R^1$ and $R^2$ may be linked to form a substituted or unsubstituted cyclic group.

3. The chelating carbene complex of claim 2, wherein the ligand precursor is of the formula

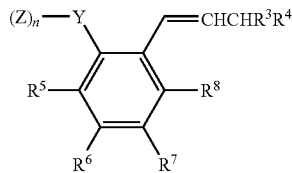

wherein

Y, Z, $R^5$, $R^6$, $R^7$, and $R^8$ are each as defined in claim 1;

n is 1, in the case of a divalent heteroatom, or 2, in the case of a trivalent heteroatom; and $R^3$ and $R^4$ are each, independently, selected from hydrogen or a substituent selected from the group consisting of alkyl, aryl, alkoxy, aryloxy, $C_2$-$C_{20}$ alkoxycarbonyl, or $C_1$-$C_{20}$ trialkylsilyl, wherein each of the substituents is substituted or unsubstituted.

4. The chelating carbene complex of claim 1, wherein $L^1$ is a phosphine or a heterocyclic carbene ligand.

5. The chelating carbene complex of claim 1, wherein Z is selected from the group consisting of hydrogen, aryl, functionalized alkyl, and functionalized aryl where the functional group(s) may be independently one or more or the following: alkoxy, aryloxy, halogen, carboxylic acid, ketone, aldehyde, nitrate, isocyanate, hydroxyl, ester, ether, amine, imine, amide, sulfide, disulfide, carbamate, silane, siloxane, phosphine, phosphate, and borate.

6. The chelating carbene complex of claim 1, wherein the functional groups of Z may be independently one or more or the following: halogen, nitrate, isocyanate, hydroxyl, ether, amine, imine, amide, sulfide, disulfide, carbamate, silane, siloxane, phosphine, phosphate, and borate.

7. The chelating carbene complex of claim 1, wherein Y is oxygen and at least one of $R^5$, $R^6$, $R^7$, and $R^8$ is heteroaryl, carbonyl, nitrile, nitro, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, or borate.

8. The chelating carbene complex of claim 1, wherein Y is oxygen and at least one of $R^5$, $R^6$, $R^7$, and $R^8$ is alkyl, aryl, functionalized alkyl, or functionalized aryl, and at least one of $R^5$, $R^6$, $R^7$, and $R^8$ is heteroaryl, carbonyl, nitrile, nitro, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, or borate.

9. The chelating carbene complex of claim 1, wherein at least one of $R^5$, $R^6$, $R^7$, and $R^8$ is alkyl, aryl, or an alkyl or alkoxy functionalized alkyl or functionalized aryl, and at least one of $R^5$, $R^6$, $R^7$, and $R^8$ is heteroaryl, carbonyl, nitrile, nitro, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, and borate.

10. A chelating carbene complex of the formula:

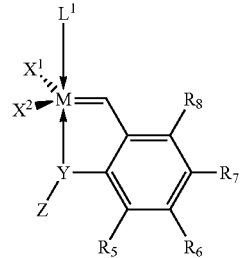

wherein $X^1$ and $X^2$ are each, independently, any anionic ligand;

$L^1$ is a neutral electron donor, and wherein any of two or three of $X^1$, $X^2$, and $L^1$ may form a multidentate ligand;

M is ruthenium or osmium;

$R^5$, $R^6$, $R^7$, and $R^8$ are each, independently, selected from the group consisting of heteroaryl, carbonyl, nitrile, nitro, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, and borate, wherein any two of $R^5$, $R^6$, $R^7$, and $R^8$ may be independently connected through hydrocarbon or functionalized hydrocarbon groups forming an aliphatic or aromatic ring;

Y is a heteroatom selected from oxygen (O), sulfur (S), nitrogen (N), or phosphorus (P); and Z is selected from the group consisting of hydrogen, alkyl, aryl, functionalized alkyl, and functionalized aryl where the functional group(s) may independently be or more or the following: alkoxy, aryloxy, halogen, carboxylic acid, ketone, aldehyde, nitrate, isocyanate, hydroxyl, ester, ether, amine, imine, amide, sulfide, disulfide, carbamate, silane, siloxane, phosphine, phosphate, and borate.

11. The chelating carbene complex of claim 10, wherein $L^1$ is a phosphine or a heterocyclic carbene ligand.

12. The chelating carbene complex of claim 10, wherein Z is selected from the group consisting of hydrogen, sec-butyl, t-butyl, neopentyl, aryl, functionalized alkyl, and functionalized aryl where the functional group(s) may independently be or more or the following: alkoxy, aryloxy, halogen, carboxylic acid, ketone, aldehyde, nitrate, isocyanate, hydroxyl, ester, ether, amine, imine, amide, sulfide, disulfide, carbamate, silane, siloxane, phosphine, phosphate, and borate.

13. The chelating carbene complex of claim 10, wherein the functional groups of Z may be independently one or more or the following: halogen, nitrate, isocyanate, hydroxyl, ether, amine, imine, amide, sulfide, disulfide, carbamate, silane, siloxane, phosphine, phosphate, and borate.

14. The chelating carbene complex of claim 10, wherein Y is oxygen and at least one of $R^5$, $R^6$, $R^7$, and $R^8$ is heteroaryl, carbonyl, nitrile, nitro, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, or borate.

15. The chelating carbene complex of claim 10, wherein Y is oxygen and at least one of $R^5$, $R^6$, $R^7$, and $R^8$ is alkyl, aryl, functionalized alkyl, or functionalized aryl, and at least one of $R^5$, $R^6$, $R^7$, and $R^8$ is heteroaryl, carbonyl, nitrile, nitro, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, or borate.

16. The chelating carbene complex of claim 10, wherein at least one of $R^5$, $R^6$, $R^7$, and $R^8$ is alkyl, aryl, or an alkyl or alkoxy functionalized alkyl or functionalized aryl, and at least one of $R^5$, $R^6$, $R^7$, and $R^8$ is heteroaryl, carbonyl, nitrile, nitro, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, and borate.

17. A chelating carbene complex of the formula:

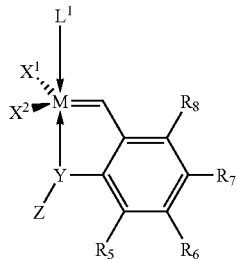

wherein
$X^1$ and $X^2$ are each, independently, any anionic ligand;
$L^1$ is a neutral electron donor, with the proviso that $L^1$ is not a heterocyclic carbene ligand, and wherein any of two or three of $X^1$, $X^2$, and $L^1$ may form a multidentate ligand;
M is ruthenium or osmium;
$R^5$, $R^6$, $R^7$, and $R^8$ are each, independently, selected from the group consisting of hydrogen, halogen, alkyl, alkenyl, alkynyl, aryl, heteroaryl, alkoxy, alkenyloxy, aryloxy, alkoxycarbonyl, carbonyl, alkylamino, alkylthio, alkylsulfonyl, nitrile, nitro, alkylsulfinyl, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, and borate, wherein any two of $R^5$, $R^6$, $R^7$, and $R^8$ may be independently connected through hydrocarbon or functionalized hydrocarbon groups forming an aliphatic or aromatic ring;
Y is a heteroatom selected from oxygen (O), sulfur (S), nitrogen (N), or phosphorus (P); and
Z is selected from the group consisting of hydrogen, alkyl, aryl, functionalized alkyl, and functionalized aryl where the functional group(s) may independently be or more or the following: alkoxy, aryloxy, halogen, carboxylic acid, ketone, aldehyde, nitrate, isocyanate, hydroxyl, ester, ether, amine, imine, amide, sulfide, disulfide, carbamate, silane, siloxane, phosphine, phosphate, and borate; with the proviso that when Z is methyl or isopropyl, at least one of $R^5$, $R^6$, $R^7$, and $R^8$ is not hydrogen and $R^6$ and $R^7$ are not connected through hydrocarbon groups forming an aromatic ring.

18. The chelating carbene complex of claim 17, wherein $L^1$ is a phosphine ligand.

19. The chelating carbene complex of claim 17, wherein Z is selected from the group consisting of hydrogen, sec-butyl, t-butyl, neopentyl, aryl, functionalized alkyl, and functionalized aryl where the functional group(s) may independently be or more or the following: alkoxy, aryloxy, halogen, carboxylic acid, ketone, aldehyde, nitrate, isocyanate, hydroxyl, ester, ether, amine, imine, amide, sulfide, disulfide, carbamate, silane, siloxane, phosphine, phosphate, and borate.

20. The chelating carbene complex of claim 17, wherein the functional groups of Z may be independently one or more or the following: halogen, nitrate, isocyanate, hydroxyl, ether, amine, imine, amide, sulfide, disulfide, carbamate, silane, siloxane, phosphine, phosphate, and borate.

21. The chelating carbene complex of claim 17, wherein Y is oxygen and at least one of $R^5$, $R^6$, $R^7$, and $R^8$ is heteroaryl, carbonyl, nitrile, nitro, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, or borate.

22. The chelating carbene complex of claim 17, wherein Y is oxygen and at least one of $R^5$, $R^6$, $R^7$, and $R^8$ is alkyl, aryl, functionalized alkyl, or functionalized aryl, and at least one of $R^5$, $R^6$, $R^7$, and $R^8$ is heteroaryl, carbonyl, nitrile, nitro, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, or borate.

23. The chelating carbene complex of claim 22, wherein at least one of $R^5$, $R^6$, $R^7$, and $R^8$ is alkyl, aryl, or an alkyl or alkoxy functionalized alkyl or functionalized aryl, and at least one of $R^5$, $R^6$, $R^7$, and $R^8$ is heteroaryl, carbonyl, nitrile, nitro, trihaloalkyl, perfluoroalkyl, carboxylic acid, ketone, aldehyde, nitrate, isocyanate, hydroxyl, ester, ether, amine, imine, amide, sulfide, disulfide, sulfonate, carbamate, silane, siloxane, phosphine, phosphate, and borate.

* * * * *